(12) United States Patent
Nogar

(10) Patent No.: US 6,248,592 B1
(45) Date of Patent: Jun. 19, 2001

(54) METHOD FOR MEASURING LEAD CONCENTRATIONS IN BLOOD

(75) Inventor: Nicholas S. Nogar, Los Alamos, NM (US)

(73) Assignee: The Regents of the University of California, Los Alamos (MX)

( * ) Notice: Subject to any disclaimer, the term of this patent is extended or adjusted under 35 U.S.C. 154(b) by 0 days.

(21) Appl. No.: 08/412,235

(22) Filed: Mar. 27, 1995

(51) Int. Cl.$^7$ .................................................. G01N 33/20
(52) U.S. Cl. ................................ 436/74; 436/73; 436/77; 436/173
(58) Field of Search ................................. 436/73, 74, 77, 436/173

(56) References Cited

PUBLICATIONS

N.S, Nogar et al. *Anal. Chem.* 1992, 64, 465–468.*
F. Hillenkamp et al. *Appl. Phys.* 1975, 8, 341–348.*
P.F. Schmidt et al. *Scanning Electron. Microsc.* 1980, 623–634.*
H. Vogt et al. *Fresenius Z. Anal. Chem.* 1981, 308, 195–200.*
R. Böhm *Fresenius Z. Anal. Chem.* 1981, 308, 258–259.*
P.F. Schmidt *Spurenelem.: Grundlagen, Aetiol., Diagn. Ther.* 1983, 12–24.*
N. Omenetto et al. *Analyst 1984*, 109, 1067–1070.*
R.W. Linton et al. Anal. Chem. 1985, 57, 440–443.*
B. Lindner et al. *Anal. Chem.* 1985, 57, 895–899.*
P.R. Flood et al. *Arch. Toxicol.* 1988, 62, 295–300.*

G.C. Turk et al. *J. Anal. At. Spectrom.* 1990, 5, 595–601.*
S,F. Durrant *Analyst* 1992, 117, 1585–1592.*
Lois Ember, "Need for Better Tests for Lead in Blood Is Urgent," Chemical & Engineering News, p. 7, Oct. 25, 1993.
Patrick J. Parsons, "Monitoring Human Exposure to Lead: An Assessment of Current Laboratory Performance for the Determination of Blood Lead," Environment Research 57, 149–162 (1992).
B. L. Fearey et al., "Pulsed Laser Resonance Ionization Mass Spectrometry for Elementary Selective Detection of Lead and Bismuth Mixtures," Analytical Chemistry 60, 1786 (1988).
I. S. Borthwick et al., "Resonant Laser Ablation—A Novel Surface Analytic Technique," Spectrochimica Acta, 47B, 1259–1265 (1992).
G. C. Eiden et al., "Resonant Laser Ablation: Semiquantitative Aspects and Threshold Effects," Michrochemical Journal 50, 289 (1994).

* cited by examiner

*Primary Examiner*—Arlen Soderquist
(74) *Attorney, Agent, or Firm*—Samuel M. Freund

(57) ABSTRACT

Method for measuring lead concentrations in blood. The present invention includes the use of resonant laser ablation to analyze $\leq 1$ $\mu L$ (or equivalent mass) samples of blood for lead content. A typical finger prick, for example, yields about 10 $\mu L$. Solid samples may also readily be analyzed by resonant laser ablation. The sample is placed on a lead-free, electrically conducting substrate and irradiated with a single, focused laser beam which simultaneously vaporizes, atomizes, and resonantly ionizes an analyte of interest in a sample. The ions are then sorted, collected and detected using a mass spectrometer.

8 Claims, 2 Drawing Sheets

METHOD FOR MEASURING LEAD CONCENTRATIONS IN BLOOD

FIELD OF THE INVENTION

The present invention relates generally to the determination of the concentration of lead in blood (BPb) and, more particularly, to the use of resonant laser ablation to quantitatively evaluate the amount of lead in a sample of blood. The invention was made with government support under Contract No. W-7405-ENG-36 between the Regents of the University of California and the U.S. Department of Energy. The government has certain rights in the invention.

BACKGROUND OF THE INVENTION

Lead poisoning is a common and potentially devastating affliction in the United States, particularly among small children. Despite advances in understanding and controlling such poisoning, including substantial reductions of lead in paints, food, water, air and gasoline, lead poisoning continues. The major remaining sources are lead-based paint in older, dilapidated housing, lead in soil and drinking water, and occupational exposure. Recent data indicate that approximately 9% of all preschool children in the United States, a total of about 1.5 million children, have already been found to have blood lead levels greater than 25 $\mu$g/dL. Among inner-city preschoolers, the problem is even more severe. More than 6 million of these children and 400,000 pregnant women are believed to have BPb levels of greater than 10 $\mu$g/dL which is the maximum level now set as safe by the Centers for Disease Control & Prevention (CDC), according to a National Research Council (NRC) panel investigation. See, e.g. "Need for better tests for lead in blood is urgent," by Lois Ember, Chemical & Engineering News, Oct. 25, 1993, page 7.

The CDC and the Environmental Protection Agency (EPA) have issued guidelines calling for intervention in any individual having a blood lead concentration (BPb) greater than 25 $\mu$g/dL, and in children having a BPb of $\geq$10 $\mu$g/dL, since in 1991 the CDC concluded that blood lead levels in excess of 10 $\mu$g/dL can cause learning and behavioral disorders in children, impair central nervous system development in fetuses, and raise the blood pressure of pregnant women. Further, according to the CDC, current analytical procedures are incapable of reliable lead quantization at these levels. That is, although it remains the best available monitoring method, the widely used finger prick test which measures the accumulation of erythrocyte protoporphyrin, a marker for lead poisoning cannot accurately measure lead at the currently acceptable level. Therefore, the NRC study urges development of more sensitive procedures to measure lead in blood and in other human biologic materials. See, e.g., Ember, supra, and "Monitoring Human Exposure to Lead: An Assessment of Current Laboratory Performance for the Determination of Blood Lead," by Patrick J. Parsons, Environmental Research 57, 149–162 (1992).

It is well known that laser resonance ionization of samples greatly enhances the sensitivity and selectivity of mass spectrometry. See, e.g. "Pulsed Laser Resonance Ionization Mass Spectrometry for Elementally Selective Detection of Lead and Bismuth Mixtures," by B. L. Fearey et al., Analytical Chemistry 60,1786 (1988). Laser ablation (evaporation/volatilization) is rapidly gaining popularity as a method of sample introduction for mass spectrometry. Several attributes are characteristic of laser ablation mass spectrometry: 1) no background is introduced due to bulk heating of the sample; 2) spatial resolution can be very good, limited only by diffraction of the incident beam (typically 1 $\mu$m in diameter); 3) little sample preparation is needed; and 4) sensitivity is excellent, the detection limit frequently falling in the femtogram to attogram (absolute) or sub-part-per-billion range.

While most laser ablation/mass spectrometry has been performed with fixed frequency lasers operating at relatively high intensities/fluences ($\geq$10$^8$W/cm$^2$;$\geq$1J/cm$^2$), there has been some recent interest in the use of tunable lasers to enhance the ionization yield of selected components in an analytical sample as well. This process, termed resonant laser ablation, is a combination of laser ablation and resonance ionization, and has been applied as a surface analytic technique to the analysis of small amounts of aluminum in steel samples, by I. S. Borthwick et al., and described in "Resonant laser ablation-a novel surface analytic technique," Spectrochimica Acta, 47B, pp. 1259–1265 (1992). Application of this technique to impurities in other solids is described in "Resonant Laser Ablation: Semiquantitative Aspects and Threshold Effects," by G. C. Eiden et al., Microchemical Journal 50, 289 (1994). Advantages of resonant laser ablation include: 1) simplification of the mass spectrum, by enhancement of signal from the analyte of interest; 2) improvement of the absolute detection limits by improving the ionization efficiency; and 3)improvement in relative sensitivity by reduction of spurious signals in the detection channel of interest (due to bleed through from adjacent mass channels or from isobaric interferences). However, no mention is made of applying resonant laser ablation to analysis of samples located exterior to a substrate and, in particular, to blood samples.

Accordingly, it is an object of the present invention to accurately, quantitatively determine lead concentration in blood samples.

Another object of the invention is to accurately, quantitatively determine lead concentration in blood samples with minimum sample preparation.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for determining the amount of lead in a liquid blood sample may include the steps of applying a known volume of blood to be investigated to a lead-free, electrically conducting substrate, allowing the blood to dry, analyzing the blood sample to exhaustion using resonant laser ablation selectively producing thereby an ion count from lead atoms present therein, and integrating the ion count, whereby the integrated ion count is a measure of the lead content.

In another aspect of the present invention, in accordance with its objects and purposes, the method for determining the amount of lead in a solid blood sample may include the steps of placing a known weight of blood to be investigated on a lead-free, electrically conducting substrate, analyzing the blood sample to exhaustion using resonant laser ablation selectively producing thereby an ion count from lead atoms present therein, and integrating the ion count, whereby the integrated ion count is a measure of the lead content.

In yet another aspect of the present invention, in accordance with its objects and purposes, the method for determining the amount of lead in a liquid blood sample may include the steps of: applying the blood sample to be investigated to a lead-free, electrically conducting substrate; drying the blood sample; analyzing a portion of the blood sample using resonant laser ablation, selectively producing thereby an ion count from lead atoms present therein; analyzing simultaneously the blood sample for sodium atom content using the same mass spectroscopy apparatus as that used in analyzing the blood sample for lead, producing thereby an ion count from sodium atoms present therein; obtaining the ratio of the ion count for lead atoms to the ion count for sodium atoms; and determining the sodium concentration in the blood sample.

In still another aspect of the present invention, in accordance with its objects and purposes, the method for determining the amount of lead in a solid blood sample may include the steps of: placing the blood to be investigated on a lead-free, electrically conducting substrate; analyzing a portion of the blood using resonant laser ablation, selectively producing thereby an ion count from lead atoms present therein; simultaneously analyzing an identical size portion of the blood sample for sodium atom content using the same mass spectroscopy apparatus as that used in analyzing the blood sample for lead, producing thereby an ion count from sodium atoms present therein; obtaining the ratio of the ion count for lead atoms to the ion count for sodium atoms; and determining the sodium concentration in the blood sample.

Benefits and advantages of the present invention include simple sample handling and preparation, great sensitivity, and the ability to analyze very small solid or liquid samples.

BRIEF DESCRIPTION OF THE DRAWINGS

The accompanying drawings, which are incorporated in and form a part of the specification, illustrate two embodiments of the present invention and, together with the description, serve to explain the principles of the invention. In the drawings.

DETAILED DESCRIPTION

Figure 1:
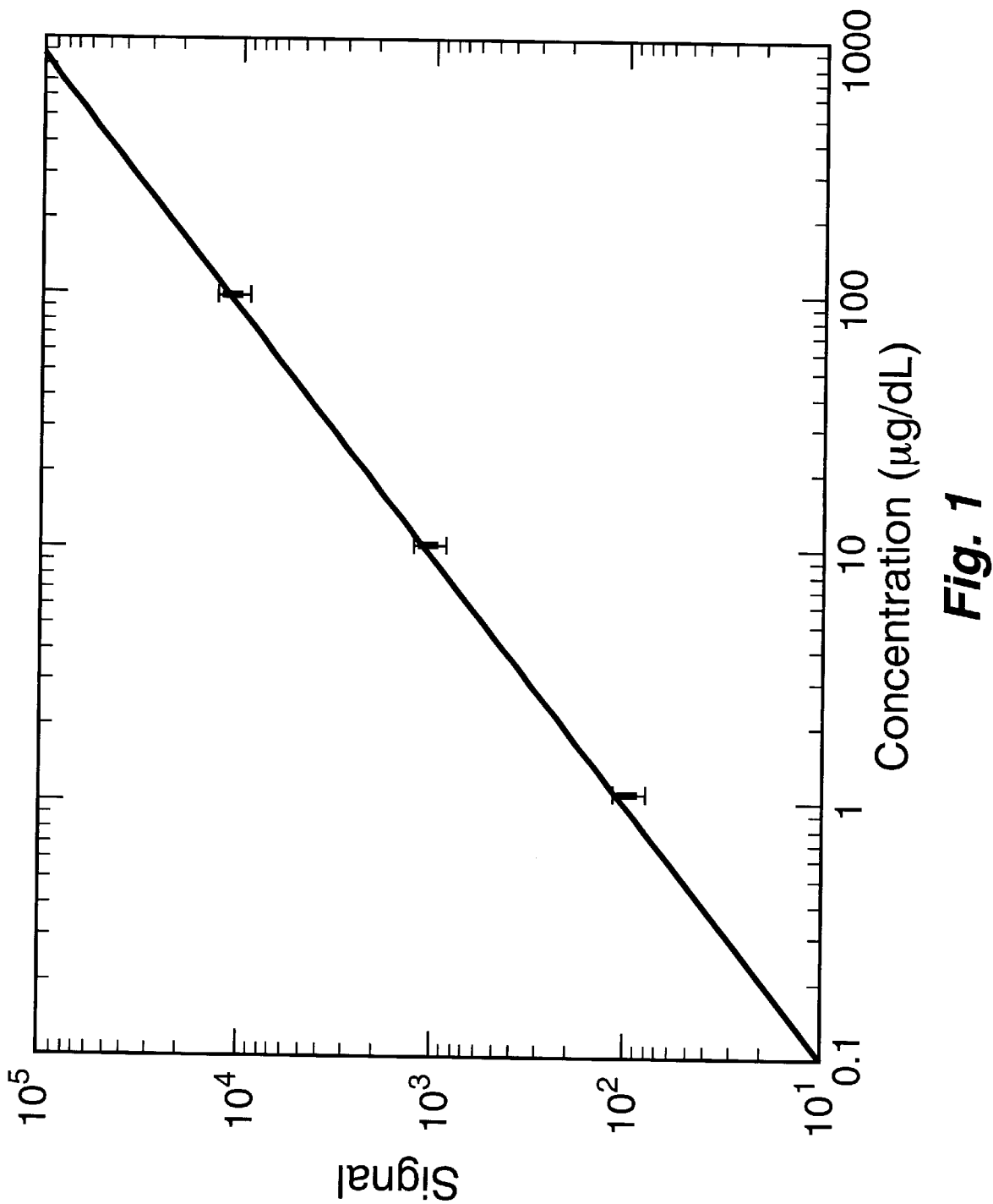
FIG. 1 shows an analytic curve for lead from lead acetate using resonant laser ablation.

Briefly, the present invention includes the use of resonant laser ablation to analyze $\leq 1$ $\mu$L (or equivalent mass) samples of blood for lead content. A typical finger prick, for example, yields about 10 $\mu$L. Solid samples may also readily be analyzed by resonant laser ablation. The sample is placed on a lead-free, electrically conducting substrate and irradiated with a single, focused laser beam which simultaneously vaporizes, atomizes, and resonantly ionizes an analyte of interest in a sample. The ionization of lead occurs through a three-photon process through a resonant intermediate state (See, e.g., B. L. Fearey et al., supra), and has been shown to be selective, and essentially interference-free. The ions are then sorted, collected and detected using a mass spectrometer. As stated above, lead concentrations at the 100 parts-per-billion level are required to be quantified. Resonant laser ablation has been demonstrated to be effective for detecting contaminants in the part-per-trillion level.

The optical source consisted of a XeCl excimer laser pumping a dye laser, the output energy of which is a few milliJoules at about 460 nm in approximately 10-ns pulses, at a repetition rate of 10 Hz. The dye laser beam was split and attenuated prior to striking the sample, so that typical incident pulse energies were between 10 and 100 $\mu$J. The ion detector was a channel electron multiplier having its output amplified, directed to a boxcar averager or digital oscilloscope, and then transferred to a microcomputer. Dye laser wavelengths were calibrated against optogalvanic spectra of Fe and U. A beam splitter was used to generate a parallel beam line for optical diagnostics (beam energy, pulse duration, and spatial profile). The spatial profile was near-Gaussian, as determined by a CCD camera and commercial beam analysis instrument. The beam was focused by a 20-cm lens and was directed to be incident on the sample surface at an angle of 11°, producing a stripe on the sample surface that was 0.34 by 1.8 mm (0.006 cm$^2$), measured at the 1/e intensity points of the beam. Continuous monitoring of the laser intensity was accomplished by directing a reflection of the incident beam through a series of neutral-density filters to a fast photodiode. The photodiode output was sent to a boxcar averager whose output was then digitized. The linearity of both the photodiode and the ion signal acquisition was carefully checked for saturation of any of the elements involved in obtaining a signal versus laser intensity plot (photodiode response, boxcar linearity, and ion detector linearity).

The mass spectrometer, resolution of about 100 (m/$\Delta$m), was a modified time of flight instrument consisting of a turbo pumped five-way cross with an attached 0.4 -m flight tube and a channeltron detector assembly. The source was typically evacuated to is 1–2×10$^{-7}$ Torr during data acquisition. The samples were mounted on a rotation/translation vacuum feedthrough manipulator via an electrically insulating connection allowing biasing of the sample. Ions were accelerated from the target, biased at 300–500 VDC positive, to the first plate of the extractor, biased at 0–200 VDC negative, and subsequently injected into the drift region of the spectrometer. Inhomogeneous fields in the target-to-first-extractor plate region combined with the angular spread of the ions reduces the ion sampling efficiency relative to a source geometry in which the target surface is coplanar with the first extractor plate.

Reference will now be made to the present preferred embodiments of the invention, examples of which are illustrated in the accompanying drawings. Turning to FIG. 1, an analytic curve of the detected signal as a function of lead concentration, is shown. One microliter samples of lead acetate solution having concentrations between 1 and 100 $\mu$g/dL were pipetted onto electronics-grade silicon substrates. The samples were permitted to dry in air for about 5 minutes, after which they were mounted on a rotatable-push/pull vacuum feedthrough and placed in a vacuum chamber. Typical pumpdown times were approximately 30 min. Analysis time to achieve complete exhaustion of the sample was about 10 min. Ionization efficiency (ions detected/atoms in the sample) was found to be $\approx 10^{-6}$. Actual blood samples have not yet been analyzed using the present method.

Figure 2:
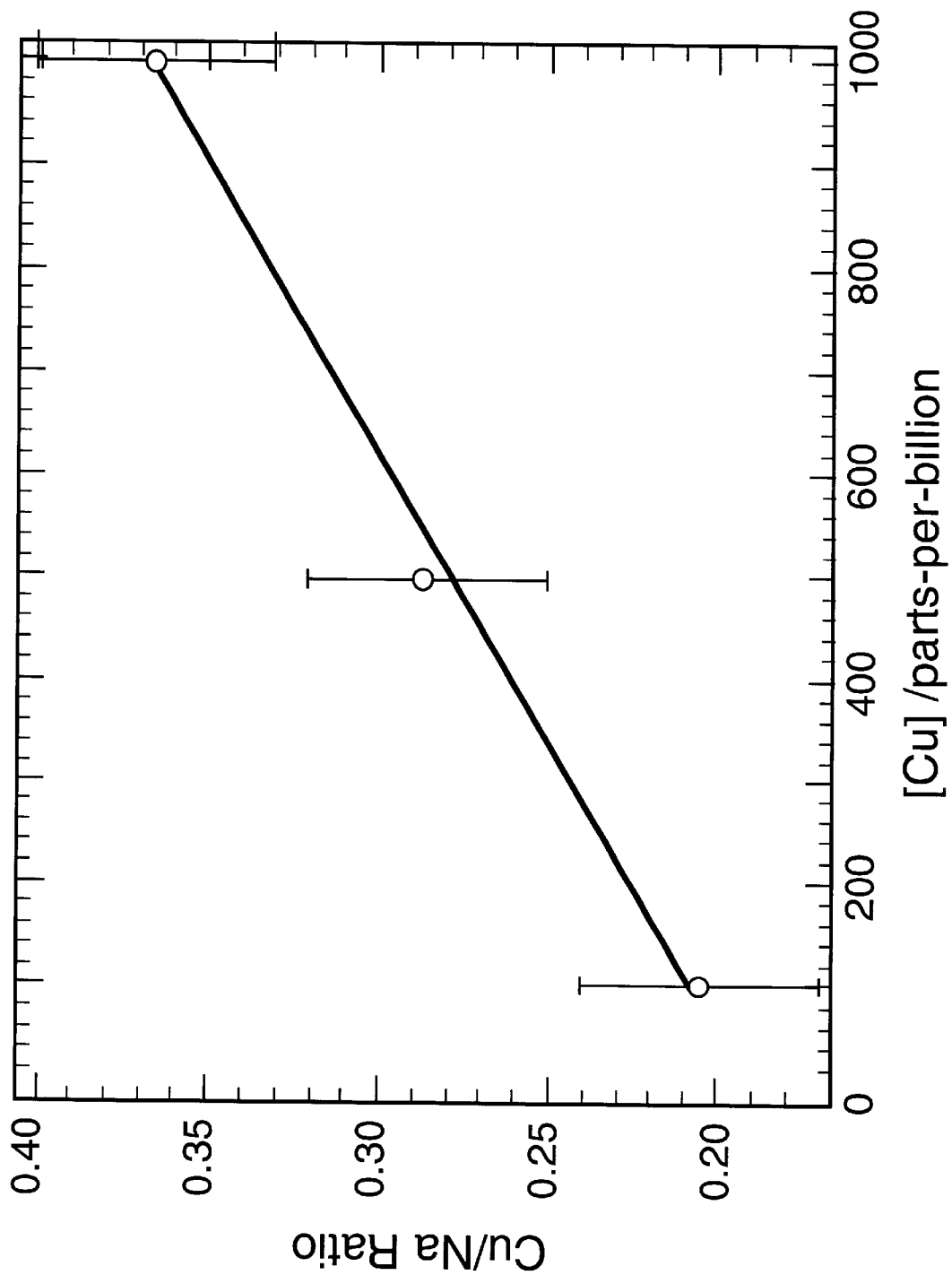
FIG. 2 shows an analytic curve for copper in solution as an ethylenediaminetetraacetate (EDTA) complex.

It has also been demonstrated that by ratioing the analyte signal to an internal standard (Pb against Na, for example, in the case of blood) the precision of the measurements may be improved. Moreover, and perhaps more importantly, the sample does not have to be analyzed to exhaustion as would be necessary when making absolute measurements as long as the two ions are counted simultaneously. FIG. 2 illustrates the results of this procedure for copper, where a resonant copper signal (at ppb levels) is ratioed against a nonresonant sodium level (part-per-thousand level) in the sample. Samples having a known concentration of copper in aqueous solution as the EDTA complex thereof, were aspirated (pneumatic nebulizer) onto a silicon wafer, dried, and inserted into the mass spectrometer, in a similar manner to that described hereinabove for lead (pressure$\approx 10^{-7}$ Torr, laser energy$\approx 15$ $\mu$J, and spot size $\approx 0.002$ cm$^2$). The laser was tuned to a copper transition, and mass spectra acquired. The copper concentration in different samples was ratioed to the (constant) sodium concentration in each sample. Thus, if one knows the sodium concentration a priori, as would be the situation for blood plasma, the trace metal (Pb) concentration is obtainable by internal calibration.

In the analysis of blood samples, several steps would be employed: 1) sample acquisition; 2) sample handling and preparation; and 3) measurement. Because of the substantial sensitivity of the resonant laser ablation, small samples may be used. Current blood lead analyses require several mL of blood generally obtained from a venipuncture in order to provide sufficient sample for accurate analysis. The method of the present invention can be made on a 10 $\mu$L sample from a finger prick. This is an important benefit, especially when dealing with children. It is anticipated that glass hematocrit tubes containing sodium heparin to prevent clotting, will be employed for sampling. Blood samples will be applied directly to a high-purity substrate, as was done for the lead acetate samples actually tested. The substrates must be electrically conducting and lead-free. The current substrate of choice is electronics-grade silicon wafers, which are ultrahigh purity, extremely reproducible from batch-to-batch, and relatively inexpensive. In some situations, the blood sample will be treated with nitric acid after placement on the wafer, and perhaps overcoated with a graphite layer to improve atomization, and permitted to dry in a clean laminar airflow. This procedure minimizes sample handling, and the potential for sample contamination, which limits the accuracy of current atomic absorption analyses. Multiple samples may be mounted on a sample carousel, and inserted through a vacuum load-lock into the vacuum chamber containing the mass spectrometer. Multiple-sample capability is important in order to maintain high sample throughput, and minimize cost-and-time per sample. Ions are typically detected at 1–100 per laser pulse, permitting the detector and electronics to operate in their linear range. Signal processing is achieved using a transient digitizer and microcomputer. Samples may be analyzed to exhaustion, and the integrated ion signal therefrom is an accurate measure of the lead content of the sample, or lead ion signals may be ratioed against sodium ion signals simultaneously obtained from the same sample, as an internal calibration. For 10 $\mu$L samples, about 15 min. will be required for an analysis. Calibrations may be performed periodically using stable isotopes and isotope dilution procedures.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining the amount of lead in a liquid blood sample, which comprises the steps of:
   a. applying a known volume of blood to be investigated to a lead-free, electrically conducting substrate;
   b. drying the blood so applied;
   c. analyzing the blood sample to exhaustion using resonant laser ablation, selectively producing thereby an ion count from lead atoms present therein; and
   d. integrating the ion count; whereby the integrated ion count is a measure of the lead content.

2. The method for determining the amount of lead in a liquid blood sample as described in claim 1, wherein the lead-free, electrically conducting substrate includes ultra-high purity silicon wafers.

3. The method for determining the amount of lead in a liquid blood sample as described in claim 1, further comprising the step of treating the blood with nitric acid after said step of applying the known volume of blood to be investigated to a lead-free, electrically conducting substrate.

4. The method for determining the amount of lead in a liquid blood sample as described in claim 1, further comprising the step of adding an anticoagulant to the blood sample before said step of applying the blood to be investigated to the substrate.

5. A method for determining the amount of lead in a liquid blood sample, which comprises the steps of:
   a. applying the blood sample to be investigated to a lead-free, electrically conducting substrate;
   b. drying the blood sample;
   c. analyzing a portion of the blood sample with a mass spectroscopy apparatus using resonant laser ablation, selectively producing thereby an ion count from lead atoms present therein;
   d. simultaneously analyzing the blood sample for sodium atom content using the same mass spectroscopy apparatus as that used in step c, producing thereby an ion count from sodium atoms present therein;
   e. obtaining the ratio of the ion count for lead atoms to the ion count for sodium atoms; and
   f. determining the sodium concentration in the blood sample.

6. A method for determining the amount of lead in a solid blood sample, which comprises the steps of:
   a. placing a known weight of blood to be investigated on a lead-free, electrically conducting substrate;
   b. analyzing the blood so placed to exhaustion using resonant laser ablation, selectively producing thereby an ion count from lead atoms present therein; and
   c. integrating the ion count; whereby the integrated ion count is a measure of the lead content.

7. The method for determining the amount of lead in a solid blood sample as described in claim 6, wherein the lead-free, electrically conducting substrate includes ultra-high purity silicon wafers.

8. A method for determining the amount of lead in a solid blood sample, which comprises the steps of:
   a. placing the blood to be investigated on a lead-free, electrically conducting substrate;
   b. analyzing a portion of the blood sample with a mass spectroscopy apparatus using resonant laser ablation, selectively producing thereby an ion count from lead atoms present therein;
   c. analyzing an identical size portion of the blood sample for sodium atom content using the same mass spectroscopy apparatus as that used in step b, producing thereby an ion count from sodium atoms present therein;
   d. obtaining the ratio of the ion count for lead atoms to the ion count for sodium atoms; and
   e. determining the sodium concentration in the blood sample.

* * * * *